United States Patent [19]

Leroux

[11] Patent Number: 5,880,845
[45] Date of Patent: Mar. 9, 1999

[54] APPARATUS FOR MEASURING THE PHOTOMETRIC AND COLORIMETRICS CHARACTERISTICS OF AN OBJECT

[75] Inventor: Thierry Leroux, Calvados, France

[73] Assignee: ELDIM, Caen, France

[21] Appl. No.: 866,508

[22] Filed: May 30, 1997

[30] Foreign Application Priority Data

May 31, 1996 [FR] France ................................. 96 06731

[51] Int. Cl.⁶ ................................................. G01B 11/24
[52] U.S. Cl. ........................... 356/376; 356/372; 356/371; 356/73
[58] Field of Search ............................. 356/73, 376, 372, 356/371

[56] References Cited

U.S. PATENT DOCUMENTS

| | | | |
|---|---|---|---|
| 3,572,885 | 3/1971 | Reinheimer et al. | 350/14 |
| 4,512,640 | 4/1985 | Nihoshi | 350/510 |
| 4,870,263 | 9/1989 | Deutsch | 250/201 |
| 5,106,183 | 4/1992 | Yoder, Jr. | 356/376 |
| 5,182,614 | 1/1993 | Lill | 356/376 |
| 5,477,332 | 12/1995 | Stone et al. | 356/371 |

*Primary Examiner*—Frank G. Font
*Assistant Examiner*—Reginald A. Ratliff
*Attorney, Agent, or Firm*—Seidel Gonda, Lavorgna & Monaco, PC

[57] ABSTRACT

Apparatus comprising a measurement lens (2) forming the image of the Fourier transform (102) of the elementary area (101) in its image focal plane (Fi), a transfer lens (3) forming the image of the elementary area on a sensor (4) formed by detectors (4i,j), a diaphragm (5) for defining the aperture of the elementary area (101), and a processing circuit (6).

The lens (2) producing the Fourier transform is associated with a field lens (10), the combination of these two means (2, 10) and of the circular aperture of diameter (d) which is defined by the diaphragm (5) making it possible, for any light beam having an angle of incidence θ and an angle of azimuth ψ, to select a measurement area of elliptical shape on the object (1) analyzed.

6 Claims, 4 Drawing Sheets

APPARATUS FOR MEASURING THE PHOTOMETRIC AND COLORIMETRICS CHARACTERISTICS OF AN OBJECT

The present invention relates to an apparatus for measuring the photometric and colorimetric characteristics of an object, especially of a liquid-crystal screen, in order to determine the characteristics of an elementary area of the object in the direction of observation of this elementary area, which apparatus comprises:

- a measurement lens producing the Fourier transform (angular intensity distribution) of the elementary area in its image focal plane;
- a transfer lens forming the image of this distribution on a sensor composed of a set of detectors, each detector giving an electrical signal corresponding to the light intensity of the elementary area for a given angular coordinate;
- a diaphragm lying in the path of the light beam in order to define the aperture of the elementary area; and
- a processing circuit which receives the electrical signals from each detection cell of the sensor.

Conoscopic methods and apparatuses have been the subject of numerous publications, in particular documents FR 87 04 944 and FR 95 00 118 as well as JP 34858 and JP-5-288 638. However, these known solutions raise several kinds of problems:

- the gain of the system depends strongly on the angle, whether or not the specimen examined is itself a light emitter;
- the measurements must be rapid for industrial production applications.

The first drawback is easily explained since the area of analysis is optically conjugate with the diaphragm with respect to the measuring lens (documents FR-87 04 944, FR-95 00 118 and JP-5-2 88638).

In other words, these analysis apparatuses, which are especially applied to determining the photometric or colorimetric characteristics of display screens, and in particular liquid-crystal display screens, are useful, but the optical system does not take into account the decrease in the cross-section of the beam emitter by the elementary area of the object analysed, which is a function of the angle of inclination of the beam; in fact, the cross-section of this beam, making an angle $\theta$ with respect to the normal to the elementary emitting area of the object analysed, varies in the ratio $1:\cos\theta$. The apparent area, which has been analysed, thus varies within very wide limits depending on the analysis angle $\theta$. Under these conditions, it is necessary to correct the results of the analyses, that is to say to process the signals delivered by the sensor using corrective terms. In point of fact, this involves using extensive means, especially in terms of computation, which complicate the apparatus and considerably slow down the analysis and which above all reduce the quality of the results on account of the decrease in the signal/noise ratio as the angle of incidence of the beam increases.

The object of the present invention is to remedy these drawbacks and is intended to create an apparatus for the photometric and colorimetric analysis of a light-emitting area, and in particular of a screen such as a liquid-crystal screen, working in transmission mode or in reflection mode, which enables accurate analyses to be carried out rapidly.

For this purpose, the invention relates to an apparatus of the type defined hereinabove, characterized in that:

- the lens producing the Fourier transform is combined with a field lens;
- the combination of these two optical systems and of the circular aperture of diameter (d) which is defined by the diaphragm makes it possible, for any light beam having an angle of incidence $\theta$ and an angle of azimuth $\psi$, to select a measurement area of elliptical shape on the object analysed,
- this elliptical area having a minor axis of about (D) and a major axis of about (D/cos$\theta$), such that the product of the minor axis multiplied by the major axis varies as $1/\cos\theta$.
- (D) and (d) being related by the magnification of the optical system consisting of the measurement lens and the field lens,
- the major axis lying in the plane passing through the axis of the optical system and the angle ray emitted by the centre of the elliptical area.

This analysis apparatus makes it possible, because of the design of the lens, to free the signals obtained from the cos$\theta$ coefficient (or the inverse of this coefficient) depending on the angle of inclination of the light beams analysed.

This represents a considerable simplification of the analysis since the results collected by the sensor, which is preferably a charge-coupled device (CCD) sensor, are delivered directly. These results are not only directly exploitable but their signal/noise ratio is markedly improved compared with the signals and results obtained using known apparatuses.

According to another characteristic, the path of the light rays comprises a wavelength-selective filter or a filter which is selective over a group of wavelengths or a polarizing filter, thereby allowing selective analysis which is limited, for example, to the wavelengths perceptible by the eye.

According to another characteristic, the path of the light rays is provided with a slit defining a line of analysis, especially an azimuthal line.

Depending on its orientation, this slit allows analysis of the object along a line of a given azimuth, thereby speeding up the analysis, which is then limited to a line of cells and not to a matrix of cells of the sensor.

The analysis apparatus receives the rays emitted by the object if the latter is an emitter.

It may also be advantageous to analyse the reflection characteristics of the object. To do this, it is necessary to illuminate it in a precise manner in order to allow significant and reproducible analysis.

For this purpose, the apparatus comprises an illumination device formed by a light source, consisting of controlled light elements, lying in the image focal plane of the lens, conjugate with the focal plane of the object, and illuminating the analysed elementary area of the object with a number of light beams, of constant cross-section defined by the illuminating diaphragm, through the lens.

It is particularly advantageous for the apparatus to include a semi-transparent mirror for shifting the illumination source sideways and for letting the analysis light rays, emitted by the elementary emitting area of the object, through it.

This analysis using illumination of the object relates to the study of the reflective characteristics of the object but also to that of the influence of unwanted illumination which affects, for example, the legibility of the object, which is generally a screen.

The present invention will be described below with the aid of an illustrative embodiment shown diagrammatically in the appended drawings, in which.

Figure 3:
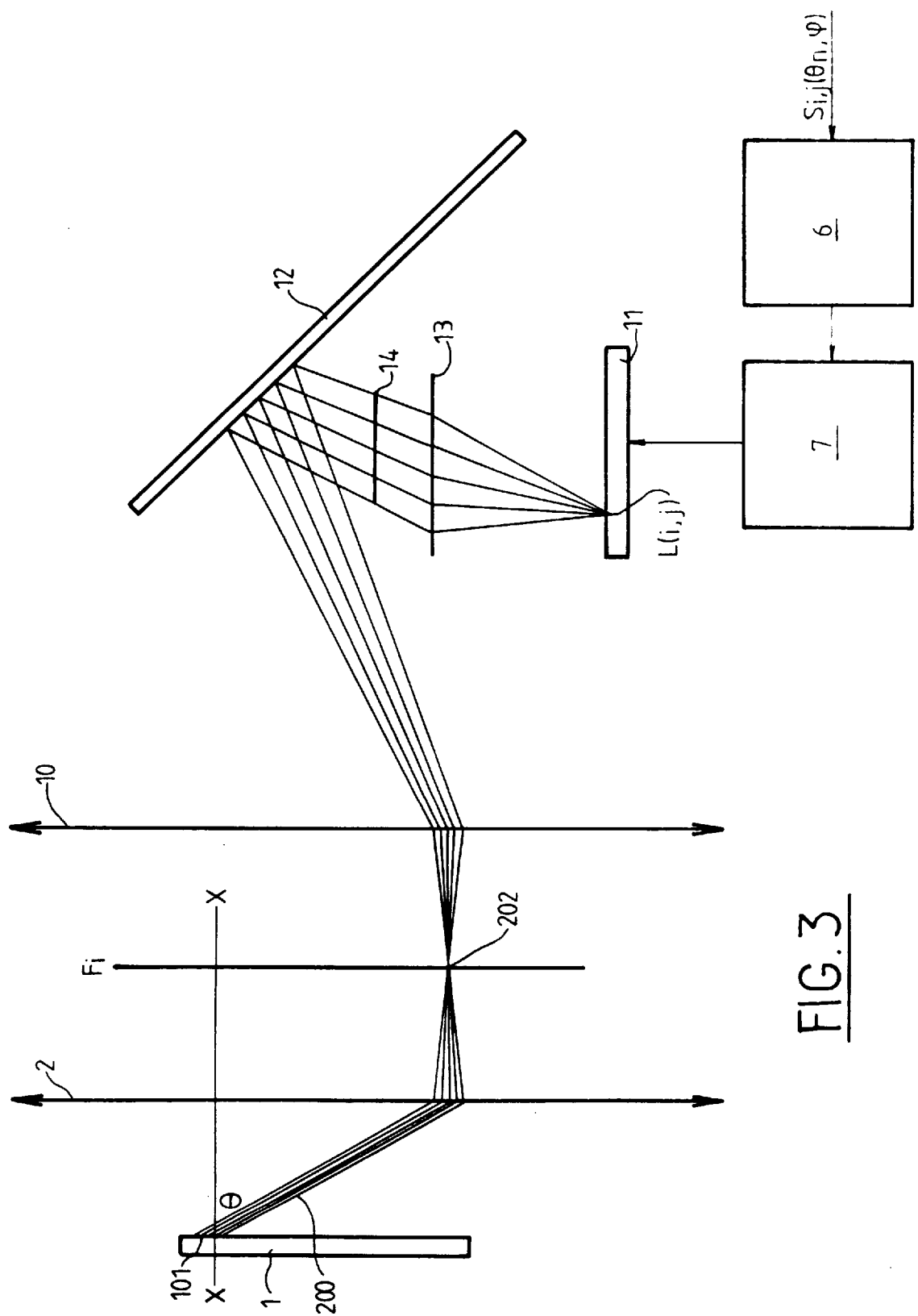
Figure 4:
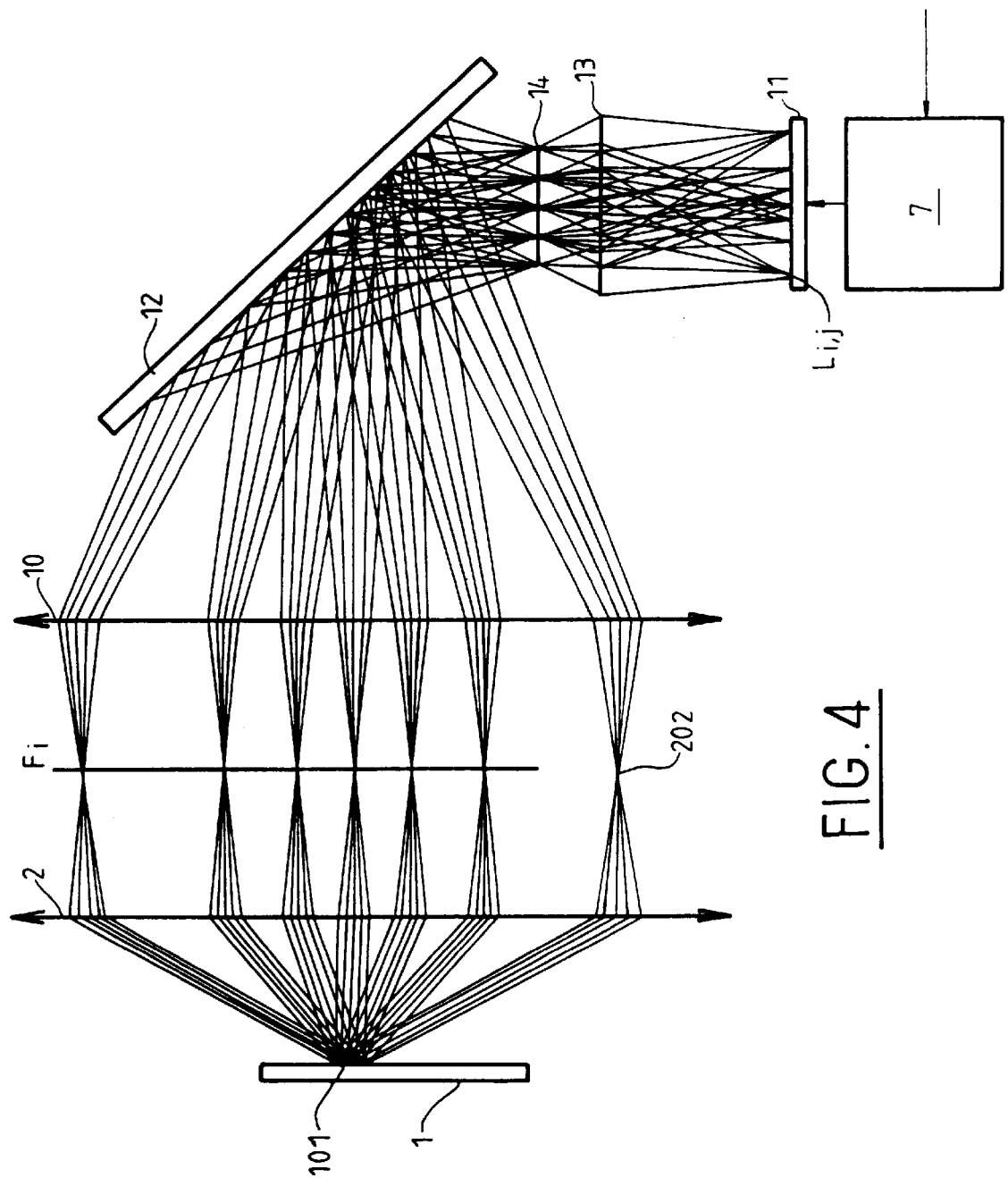

FIG. 3 diagrammatically shows the equipment for illuminating an elementary area of an object analysed;

FIG. 4 is a view similar to that in FIG. 3, but showing the illumination of the elementary area of the object by various beams of different angles of incidence with respect to the elementary area of the object.

Figure 1:
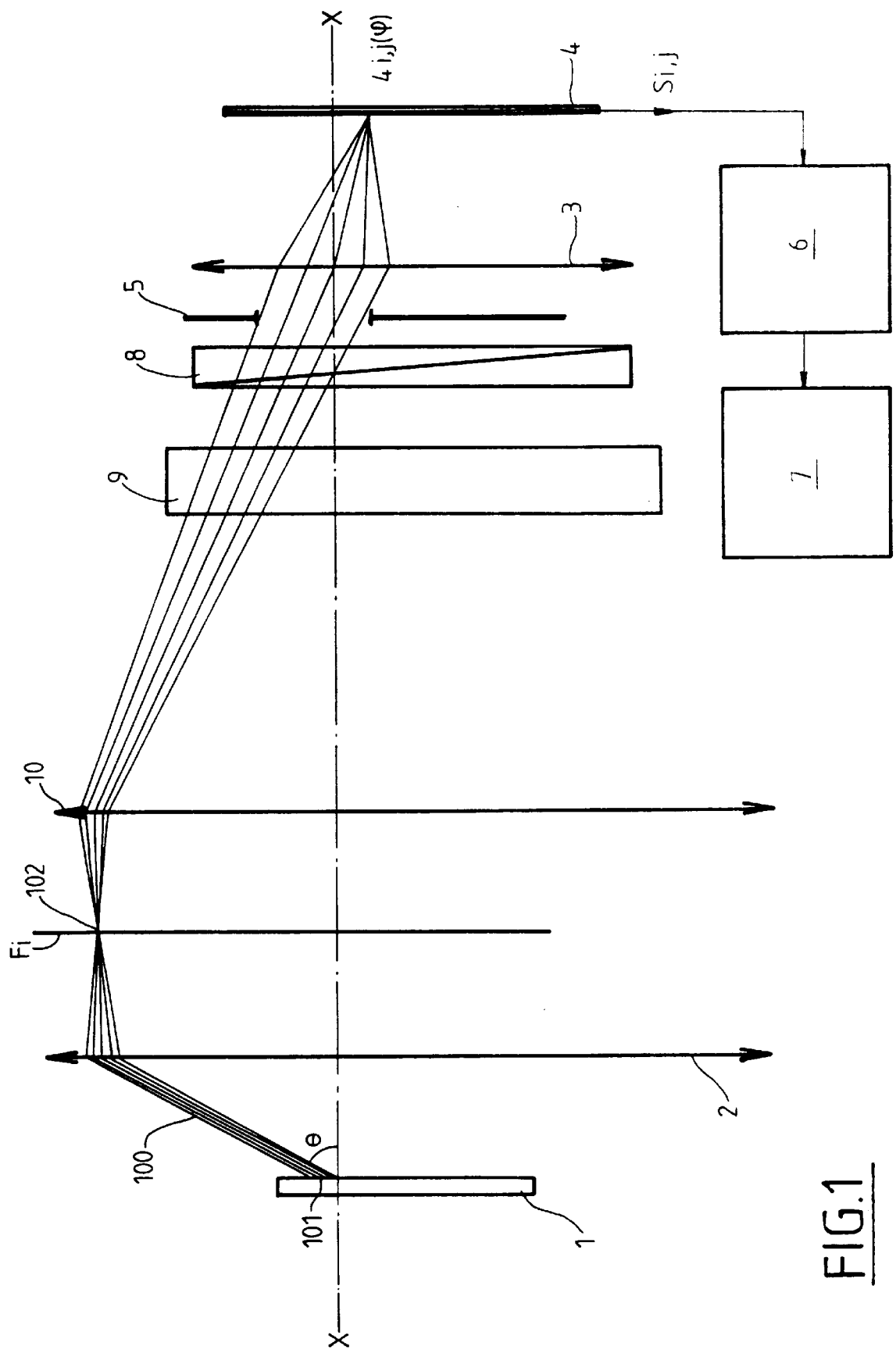
FIG. 1 shows the measurement apparatus according to the invention with the trace of a beam of parallel rays emitted by an elementary area of the object analysed.

According to FIG. 1, the apparatus according to the invention is for measuring the photometric and colorimetric characteristics of an object 1. The object 1 is, for example, a liquid-crystal screen and its characteristics are measured on elementary areas covering the entire object or part of it.

The apparatus comprises an lens 2 whose object focal plane receives the object 1 analysed. This lens 2 is followed by a transfer lens 3 which gives, from the Fourier transform for a given angular coordinate in the plane Fi, an image on the sensor 4. A diaphragm 5 defines a circular aperture of diameter d, delimiting on the object 1, in conjunction with the lens 2 and the field lens 10, an elementary emitting area 101. The diaphragm 5 also defines the beam 100 emitted by the elementary area 101 towards the lens 2 and the angle θ of the beam with the axis XX of the system.

The diaphragm 5, preferably located upstream of the transfer lens 3, may be preceded by a filter 8 which lets through only a certain wavelength or group of wavelengths. It may also be a polarizing filter.

Finally, the apparatus may comprise a shutter 9 which makes it possible to define a time during which the sensor 4 or its detection cells $4i,j$ are illuminated. Each cell receives the flux from the elementary area 101 of the object 1 passing via the beam 100 emitted in the direction θ.

The two main functions of the lens 2 are to define, in conjunction with the lens 10 and the diaphragm 5, an elementary area 101 which is optically conjugate with the diaphragm 5, and to deliver, in the plane Fi, an image representative of the angular distribution of the light emitted by the object 1. The major axis of this elliptical elementary area 101 lies in the plane of FIG. 1 and the minor axis is perpendicular to the plane of FIG. 1.

More specifically, the lens 2 defines an elliptical elementary area 101, the minor axis of which is about D and the major axis of which is about $D/\cos\theta$:

D is the conjugate measurement of the diameter d of the diaphragm S through the optical system, these two quantities being related by the magnification G.

More specifically, the major axis of the elliptical elementary area 101 lies in the plane passing through the optical axis XX and through the ray of the beam 100 passing through the centre of the elliptical area 101 (this ray is contained in the plane of FIG. 1).

The focal plane Fi therefore contains a plane image of the light intensity distribution emitted by the object 1.

The apparatus is completed by a field lens 10 which gives a real image of the object 1 in the plane of the diaphragm 5, so that it is possible to step down the light beam and thus obtained, in return, the elementary area 101 for analysis.

The image formed in the plane Fi is transferred by the lenses 10 and 3 to the sensor 4. Each detection cell $4i,j$ of the sensor 4 is directly associated with an emission direction characterized by the angle of incidence θ and the angle of azimuth ψ of a beam 100 emitted by a surface 101.

When these angles change, the elementary sensor receiving the light beam also changes.

Under these conditions, it is particularly advantageous for the sensor 4 to be a CCD sensor which makes it possible to collect the signals $Si,j$ associated with each elementary cell $4i,j$ of the sensor, that is to say the signals $Si,j$ directly associated with each angular position of the beam 100 emitted by the object 1.

Figure 2:
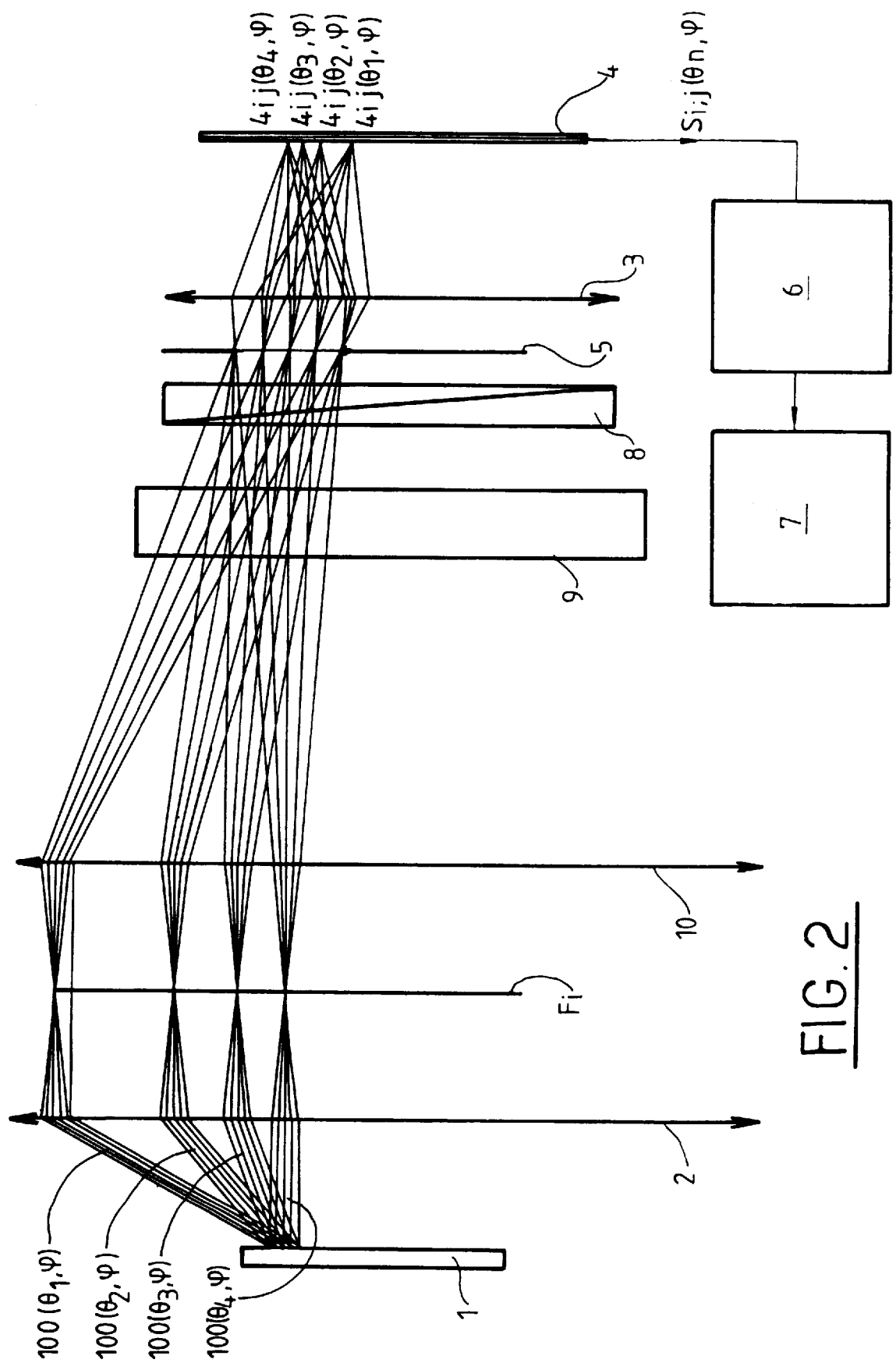
FIG. 2 shows the apparatus in FIG. 1, but diagrammatically indicating various beams, of different angles, emitted by the same elementary area of the object analysed.

FIG. 2 shows this situation diagrammatically; the measurement apparatus is the same as that in FIG. 1; only a few additional beams $100(\theta_1,\psi)$, $100(\theta_2,\psi)$, $100(\theta_3,\psi)$ and $100(\theta_4,\psi)$ associated with the cells $4i,j(\theta_1,\psi)$ ... $4i,j(\theta_4,\psi)$ have been traced.

These cells of the sensor 4 then deliver a series of signals designated generally by the reference $Si,j(\theta_n,\psi)$.

This FIG. 2 also shows that the beams $100(\theta_n,\psi)$, the axis of which lies in the plane of FIG. 2 (the plane corresponding to the angle of azimuth ψ), necessarily converge on the cells $4i,j(\theta_n,\psi)$, of the sensor 4, which also lie in the plane of FIG. 2, that is to say are aligned on a straight-line segment.

FIGS. 1 and 2 show the use of the measurement apparatus for analysing the light beams of angle θ which are emitted by the object 1.

For such an analysis to be possible, it is necessary for the object 1 to be photoemissive or for it to reflect the incident light.

It may also be advantageous to measure the optical reaction of an object 1 which is itself an emitter and which receives stray illumination.

FIG. 3 shows an apparatus according to the invention which corresponds to that described above and is provided with means enabling the object 1 to be illuminated.

In this figure, only the main elements of the apparatus used for the illumination have been shown; these elements bear the same references as in the previous figures.

To illuminate the object 1 with a beam 200 of angular position (θ,ψ), the apparatus comprises an illumination device formed by a light source 11 composed of light elements $Li,j$ which are distributed in a line, for example in the plane of the figure, or in a matrix (two-dimensional distribution). These light elements $Li,j$ are controlled by a control device, such as a microcomputer 7, which receives and processes, for example, the signals resulting from the signals $Si,j(\theta_n,\psi)$ delivered by the processing circuit 6.

This makes it possible to control the illumination of the elementary area 101, or more generally of the object 1, as a function of an analysis program which, where appropriate, takes into account results derived from the signals $Si,j(\theta_n,\psi)$ delivered by the sensor 4.

The illumination source 11 lies in the image focal plane of the lens 2 (taking into account the field lens 10).

In fact, in order to clear the area of the apparatus around the optical axis XX and allow free passage of the light beams emitted by the object 1, the light source 11 is shifted to the side by means of a semi-transparent mirror 12.

The illumination device also comprises a lens 13 and a diaphragm 14 so as to form a converging light beam in the image focal plane Fi of the lens 2, thus giving a beam of parallel rays 200 of angular position (θ,ψ) striking the elementary area 101.

The angle of incidence θ depends on the situation of the controlled light element $Li,j$ delivering the beam.

The diaphragm 14 is a circular diaphragm so that the beam emerging from the lens 2 benefits from the reciprocal optical characteristics of the lens 2, such as those defined above in the case of the beam emitted by the object 1.

The angular position (θ,ψ) for illuminating the elementary area 101 is chosen as a function of the analysis program to be carried out. This program may, for example, consist in analysing the object 1, as was described with regard to FIGS. 1 and 2, according to various angles $\theta_i$, firstly without an illumination source and them with an illumination source delivering a light beam of angular position (θ,ψ). This angle may also be modified during analysis by the control circuit 7 which employs various light elements $Li,j$ of the light source 11.

FIG. 4 shows diagrammatically the illumination of the elementary area 101 in different illumination directions, that is to say by activating different light element Li,j of the light source 11 in order to reproduce a given illumination distribution. The various elements shown in FIG. 4 bear the same reference numbers as in the previous figures.

I claim:

1. Apparatus for measuring the photometric and colorimetric characteristics of an object, especially of a liquid-crystal screen, in order to determine the characteristics of an elementary area (101) of the object (1) in the direction of observation of this elementary area (101), which apparatus comprises:

a measurement lens (2) producing the Fourier transform (angular intensity distribution) (102) of the elementary area (101) in its image focal plane (Fi);

a transfer lens (3) forming the image of this angular intensity distribution on a sensor (4) composed of a set of detectors (4$i,j$) each detector giving an electrical signal (S$i,j,\psi$) corresponding to the light intensity of the elementary area (101) for a given angular coordinate;

a diaphragm (5) lying in the path of the light beam in order to define the aperture of the elementary area (101);

a processing circuit (6) which receives the electrical signals from each detection cell (4$i,j$) of the sensor (4), which apparatus is characterized in that:

the lens (2) producing the Fourier transform is associated with a field lens (10);

the combination of these two optical means (2, 10) and of the circular aperture of diameter (d) which is defined by the diaphragm (5) makes it possible, for any light beam having an angle of incidence $\theta$ and of azimuth $\psi$, to select a measurement area of elliptical shape on the object (1) analysed, this elliptical area having a minor axis of about (D) and a major axis of about (D/cos$\theta$), such that the product of the minor axis multiplied by the major axis varies as 1/cos$\theta$, the quantities (D) and (d) being related by the magnification of the optical system formed by the measurement lens (2) and the field lens (10);

the major axis lying in the plane passing through the axis of the optical system and the ray of angle ($\theta$) emitted by the centre of the elliptical area (101).

2. Apparatus according to claim 1, characterized in that the path of the light rays comprises a wavelength-selective filter (8) or a filter which is selective over a group of wavelengths or a polarizing filter.

3. Apparatus according to claim 1, characterized in that the path of the light rays is provided with a slit (10) defining a line of analysis, especially an azimuthal line, of angle ($\psi$).

4. Apparatus according to claim 1, characterized in that it comprises an illumination device (11) formed by a light source, consisting of controlled light elements, lying in a conjugate plane of the image focal plane of the lens (2) and illuminating the object (1) with a group of light beams, of constant cross-section defined by the illuminating diaphragm, through the lens (2).

5. Apparatus according to claim 4, characterized in that it comprises a semi-transparent mirror (12) for shifting the illumination source (11) away from the optical axis and for letting the analysis, light rays, emitted by the object (1), through it.

6. Apparatus according to claim 4, characterized in that the light source (11) is controlled from a microprocessor (7), especially depending on the results of the analysis (6) of the signals (S$i,j,\psi$) delivered by the sensor (4), in order to provide selective illumination in a given direction or according to a given illumination distribution, depending on the type of analysis to be carried out on the object (1).

* * * * *